United States Patent
Chambre

(10) Patent No.: US 10,362,971 B1
(45) Date of Patent: Jul. 30, 2019

(54) FINGERPRINT POWDER

(71) Applicant: AIR SCIENCE USA LLC, Ft. Meyers, FL (US)

(72) Inventor: Paul Chambre, Fort Myers, FL (US)

(73) Assignee: AIR SCIENCE USA LLC, Fort Myers, FL (US)

(*) Notice: Subject to any disclaimer, the term of this patent is extended or adjusted under 35 U.S.C. 154(b) by 0 days.

(21) Appl. No.: 15/585,490

(22) Filed: May 3, 2017

Related U.S. Application Data

(62) Division of application No. 14/682,984, filed on Apr. 9, 2015, now Pat. No. 9,750,436.

(60) Provisional application No. 61/978,576, filed on Apr. 11, 2014.

(51) Int. Cl.
| | | |
|---|---|---|
| C08F 122/32 | (2006.01) | |
| C08J 3/12 | (2006.01) | |
| A61B 5/1172 | (2016.01) | |
| C09D 5/03 | (2006.01) | |

(52) U.S. Cl.
CPC .......... A61B 5/1172 (2013.01); C08F 122/32 (2013.01); C08J 3/12 (2013.01); *C08J 2335/04* (2013.01)

(58) Field of Classification Search
CPC .................................................. A61B 5/1132
USPC ........................................................ 528/232
See application file for complete search history.

(56) References Cited

U.S. PATENT DOCUMENTS

| | | |
|---|---|---|
| 4,176,205 A | 11/1979 | Molina |
| 4,248,543 A | 2/1981 | Carrington et al. |
| 4,407,842 A | 10/1983 | Shepard |
| 4,461,235 A | 7/1984 | Morton |
| 4,504,408 A | 3/1985 | Morton |
| 4,550,041 A | 10/1985 | Thompson et al. |
| 4,556,579 A | 12/1985 | Lowell |
| 4,613,515 A | 9/1986 | Reggio |
| 4,700,657 A | 10/1987 | Butland |
| 4,719,119 A | 1/1988 | Thompson et al. |
| 4,806,380 A | 2/1989 | Sato et al. |
| 4,882,195 A | 11/1989 | Butland |
| 4,885,191 A | 12/1989 | Podszun et al. |
| 5,039,753 A | 8/1991 | Woods et al. |
| 5,143,551 A | 9/1992 | Mason, Jr. et al. |
| 5,342,645 A | 8/1994 | Eisele et al. |
| 5,348,159 A | 9/1994 | Watkin et al. |

(Continued)

OTHER PUBLICATIONS

CyanoPowder.com website, screen shot, Apr. 26, 2013.

*Primary Examiner* — Duc Truong
(74) *Attorney, Agent, or Firm* — Birch, Stewart, Kolasch & Birch, LLP

(57) ABSTRACT

Process for producing powdered polycyanoacrylate polymer by charging a reaction vessel with an aqueous mist, dripping a 2-cyanoacrylate into the reaction vessel, allowing the resulting reaction mass (polycyanoacrylate polymer) to cool, removing the polycyanoacrylate polymer from the reaction vessel, drying it, and pulverizing the dry solid into a powder. Powdered polycyanoacrylate polymer having a particle diameter in the range of from 1 to 200 microns. The particle size and shape herein contribute to uniform distribution of fumes during fingerprint capture. A high level of accuracy in fingerprint detection is provided among three distinct levels which include: (a) first level detection from ridge flow patterns such as whorl or loop; (b) second level detection from ridge flow singularities such as ridge endings and bifurcations; (c) and third level detection from pore configuration.

7 Claims, 4 Drawing Sheets

(56) References Cited

U.S. PATENT DOCUMENTS

| | | |
|---|---|---|
| 5,348,759 A | 9/1994 | Weaver et al. |
| 5,395,445 A | 3/1995 | Bohanan |
| 5,424,092 A | 6/1995 | Weaver et al. |
| 6,423,946 B1 | 7/2002 | Berka et al. |
| 6,689,826 B2 | 2/2004 | Wojciak |
| 7,182,817 B1 | 2/2007 | Weaver et al. |
| 7,279,523 B2 | 10/2007 | Ando et al. |
| 7,323,207 B2 | 1/2008 | Nichols et al. |
| 7,465,472 B1 | 12/2008 | Weaver et al. |
| 7,487,739 B1 | 2/2009 | Weaver et al. |
| 8,268,919 B2 | 9/2012 | Shimoda et al. |
| 2003/0065069 A1 | 4/2003 | Wojciak |
| 2004/0254272 A1 | 12/2004 | Ando et al. |
| 2005/0214441 A1 | 9/2005 | Ray |
| 2005/0252444 A1 | 11/2005 | Nichols et al. |
| 2006/0165871 A1 | 7/2006 | Lubbers et al. |
| 2007/0017826 A1 | 1/2007 | Tate |
| 2007/0026130 A1 | 2/2007 | Arndt |
| 2008/0020126 A1 | 1/2008 | Arndt |
| 2008/0142760 A1 | 6/2008 | Shin et al. |
| 2010/0047433 A1 | 2/2010 | Shimoda et al. |
| 2010/0048433 A1 | 2/2010 | Shimoda et al. |
| 2010/0143575 A1 | 6/2010 | Knaggs |
| 2011/0033607 A1 | 2/2011 | Pitts et al. |
| 2012/0076918 A1 | 3/2012 | Barton et al. |

FINGERPRINT POWDER

This application is a Division of U.S. patent application Ser. No. 14/682,984 filed on Apr. 9, 2015, now U.S. Pat. No. 9,750,436, which claims the benefit under 35 U.S.C. § 119(e)(1) of provisional application Ser. No. 61/978,576, filed Apr. 11, 2014, all of which are hereby expressly incorporated by reference into the present application.

FIELD OF THE INVENTION

This invention relates to the detection of fingerprints. More specifically, this invention relates to fingerprint development using a solid form of polycyanoacrylate that is vaporized and then employed to coat a substrate believed to contain a fingerprint. The invention also relates to a process for preparing the polycyanoacrylate.

BACKGROUND OF THE INVENTION

Fingerprint powders are fine powders used in dusting for fingerprints, for instance, by crime scene investigators and others in law enforcement. The process of dusting for fingerprints involves various methods intended to get the particles of the powder to adhere to residue left by friction ridge skin on the fingers, palms, or feet. Physical development of fingerprints using powders is just one of various methods used to develop fingerprints. Fingerprints often leave residues of oils in the shape of the friction ridges, but the friction ridge skin itself does not secrete oils. For this reason, some fingerprints will only leave a residue of amino acids and other compounds to which the powder does not adhere. Dusting is used as part of an array of techniques to develop fingerprints. Dusting is often used on larger areas in a crime scene which cannot be removed for analysis.

Powders may be applied with a fingerprint brush, which is a brush with extremely fine fibers designed to hold powder and deposit it gently on the fingerprint to be revealed without rubbing away the often delicate residue of the fingerprint itself. Powders may also be applied by blowing the powder across the fingerprint, or by pouring the powder onto the print, and then blowing away the excess. Historically, lycopodium powder—that is, spores of mosses, ground cedar, and the like—was used as a fingerprint powder. Modern fingerprint powders have a variety of compositions, including for example aluminum powder, aluminum flakes, and lampblack.

Factors influencing the effectiveness of fingerprint powders include fineness (the powder must be fine enough to show the detail of the fingerprint), adhesion (the powder should adhere to the residue of the fingerprint and not adhere to the rest of the surface so as to obscure the view of the print), color (the fingerprint powder should be a suitable color for the surface in question), and flowability (the powder should not cake into a solid).

Some surfaces, such as organic ones, do not lend themselves to the use of fingerprint powders, so that use of alternate methods is necessary. Other media, such as certain types of glue, can be "smoked" over these surfaces to develop the latent fingerprints thereupon. For instance, when the specimen is a metallic weapon such as a handgun or a knife, synthetic leather, or an adhesive face of an adhesive tape, dusting with powder cannot copy the fingerprint clearly. Instead, methods in which 2-cyanoacrylate is vaporized and converted via moisture on a fingerprint to a polymer have been used as a method for developing a fingerprint residue more clearly. Conventionally, such fingerprint detection has been conducted with what is, in effect, liquid cyanoacrylate glue.

The detection of fingerprint using 2-cyanoacrylate is usually carried out by means of allowing a vapor of 2-cyanoacrylate (monomer) to adhere to a fingerprint. For instance, 2-cyanoacrylate (monomer) may be sprayed onto latent fingerprints or impregnated into woven or nonwoven fabric and allowed to volatilize onto the latent fingerprints. Another known method involves simultaneous use of vapors of 2-cyanoacrylate (monomer) and a sublimation dye, to colorize the fingerprint detection when the fingerprints are present on a white or silvery colored metallic surface.

U.S. Pat. No. 8,268,919 (Shimoda) discloses the preparation of crushed powder mixtures for use in detecting fingerprints. The claims of the Shimoda patent recite a composition for detecting fingerprints, which composition comprises a 2-cyanoacrylate polymer polymerized by use of a specified type of polymerization initiator. Shimoda also discloses the use of polymers obtained by reacting a 2-cyanoacrylate with specific fluorescent colorants which act as polymerization initiators.

Weaver (U.S. Pat. No. 5,348,759) discloses a device that can be used to detect latent prints in a variety of locations, including outdoors. The device has a housing which holds a quantity of solid granulated cyanoacrylate. The Weaver patent does not provide any details regarding the nature of the solid granulated cyanoacrylate. The cyanoacrylate is placed around the periphery of the housing. One end of the housing is tapered to form a connecting tube, and the connecting tube is placed on the end of a propane torch. The torch is used to vaporize the cyanoacrylate in the housing into a vapor. The vapor is then propelled forward from the torch by the velocity of the torch exhaust gases, and projected onto the test object, which causes latent prints to appear.

SUMMARY OF THE INVENTION

The present invention provides a powdered polycyanoacrylate polymer wherein greater than 95%, preferably greater than 98%, and more preferably greater than 99% of the polymer mass comprises polymer particles having a particle diameter in the range of from 1 to 200 microns. Analysis has shown that the polycyanoacrylate polymer particles of the present invention have a variety of different shapes, including rectangular, triangular, diamond-shape, circular, cylindrical, etc. Due to the irregularity of the particles, in the context of the present invention, "particle diameter" refers to the largest measurement of a particle's cross-section. Particle diameter can be measured by manual screening or by a sieve process involving pulsation in a blender. For example, the dried polymer may be pulsed 3-5 times for 15 second bursts, at which point the dried polycyanoacrylate polymer will be pulverized to a level of 1 to 200 microns. The particles can then be sifted out of the top of the blender and manually inspected to verify particle consistency.

Preferably, the powder has a median particle diameter in the range 10 to 30 microns, more preferably in the range 15 to 25 microns, still more preferably in the range 18 to 22 microns, and most preferably of approximately 20 microns. Preferably, the powder has a mean particle diameter in the range 30 to 90 microns, more preferably in the range 45 to 75 microns, still more preferably in the range 55 to 65 microns, and most preferably of approximately 60 microns. The powdered polycyanoacrylate polymer of the invention may have one or more of the following particle size characteristics: at least 50 weight-% of the powder particles have a feret length of from 20 to 80 nanometers; at least 50 weight-% of the powder particles have a feret width of from 10 to 40 nanometers; and at least 50 weight-% of the powder particles have a rectangularity ranging from 60 to 75.

The present invention also provides a process for producing a powdered polycyanoacrylate polymer. The inventive process starts by charging a reaction vessel with a mist comprising water. The atmosphere in the reaction vessel can be typical ambient air at ambient pressure. In other words, other than controlling the temperature (as discussed below), the reaction can proceed at atmospheric pressure using ambient air. Then, methyl or ethyl 2-cyanoacrylate monomer is added to the reaction vessel by slowly dripping it into the water mist, thereby producing an exothermic reaction. The rate of the polymerization reaction should be controlled in order to bring about uniformity in the solid polymer. The rate of polymerization may be controlled by decreasing or temporarily halting the rate of addition of the methyl or ethyl 2-cyanoacrylate if the temperature in the reaction vessel becomes so high that the desired consistency of the product solid itself results in a non-uniform product. For example, is it desirable to slow or halt the addition of methyl or ethyl 2-cyanoacrylate when the temperature reaches a temperature somewhere in the range of 45-55° C., preferably in the range of 48-52° C., and most preferably if the temperature reaches 50° C. If too high a temperature is used, there is a danger that the monomer's flash point would be exceeded.

Once all of the methyl or ethyl 2-cyanoacrylate has been added, the reaction mass is allowed to cool (or remain below 50° C.). The reaction mass would not harden at too high a temperature. Subsequently, any liquid water remaining is removed from the reaction vessel, leaving polycyanoacrylate polymer adhered to the walls thereof. The polycyanoacrylate polymer is then scraped off the walls or otherwise removed from the reaction vessel and then dried, resulting in a dry solid polycyanoacrylate polymer.

Finally, the dry solid is pulverized into a powder using an industrial-grade benchtop grinder mill. The resulting powder is then separated via conventional multiple screen vibration to separate the desired sized particles from larger and smaller particles. The desired particles size ranges from 1 micron to 200 microns.

The chemical and physical characteristics of the product provided by this invention create an exceptionally stable physical construct at ambient temperature, allowing for a long shelf life, stability in processing, and ease of use during and in preparation for fuming. In a preferred embodiment of the invention, the product remains physically stable at temperatures below 220° C., thereby eliminating any concerns regarding off-gassing or material loss due to hardening.

The powdered polycyanoacrylate particles of the present invention have a very long shelf life. The shelf life of the particles of the present invention is far longer than the typical time from manufacturing to use. Liquid polycyanoacrylate immediately begins producing fumes at ambient temperatures and hardens, resulting in up to 15% material loss. Unlike liquid glue that hardens once opened, the product provided by the current invention can be openly stored in ambient conditions for an indefinite amount of time with no associated material loss and no additional storage precautions.

Due to the unique physical characteristics of the polycyanoacrylate powder, including particle size distribution and the shapes of the particles, the invention provides a high level of accuracy in fingerprint detection among three distinct levels which include: (a) first level detection from ridge flow patterns such as whorl or loop; (b) second level detection from ridge flow singularities such as ridge endings and bifurcations; (c) and third level detection from pore configuration. Specifically, the present invention enhances detection and visualization of pores which occur on the rides of each individual's fingerprints. While other technologies have sporadically elucidated such pores, the present invention provides them consistently. The particle size and shape in the present invention contribute to uniform distribution of fumes during fingerprint capture, which minimizes "over-fuming" prints, and facilitates wiping off background fuming residue from most surfaces, including metals and plastics.

It has been discovered that the powder of the present invention performs very well without adding to the powder or incorporating within the powder a colorant or fluorescent substance. However, colorants and/or fluorescent substances can be used in the present invention. More specifically, fluorescent substances, such as those described in U.S. Pat. No. 8,268,919, can be added to or incorporated within the powder by techniques known in the prior art.

Finally, the present invention is also directed to a method for detecting fingerprints comprising vaporizing the powder of the present invention in the vicinity of a substrate suspected of having fingerprints thereon and allowing the vaporized polycyanoacrylate to settle onto the substrate. The powder can be vaporized by placing the powder in an open receptacle (such as a fuming dish) which is heated (for example, by a hot plate) to a temperature at which the powder vaporizes (or forms fumes). The temperature can vary somewhat depending upon the exact constitution of the powder. However, it has been found that a fuming temperature of 220° C. is effective. The powder is heated until it is substantially fully vaporized or until sufficient powder is vaporized to detect fingerprints on a substrate being analyzed.

DETAILED DESCRIPTION OF THE INVENTION

Figure 1A:
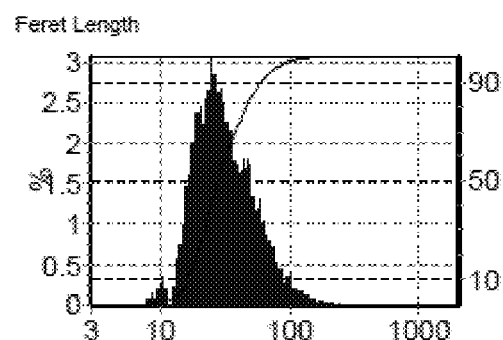
FIGS. 1A, 1B, and 1C are graphical depictions of feret length, feret width, and rectangularity of a sample of particles produced in accordance with the invention.

Methyl or ethyl 2-cyanoacrylate is generally used as the sole or primary monomer which is polymerized to make the polymer that is powdered in accordance with the present invention. Methyl cyanoacrylate has a boiling point of 48-49° C. Ethyl 2-cyanoacrylate has a flash point of 83° C. and a boiling point of 54-56° C. However, other 2-cyanoacrylates and 2-cyanomethacrylates, such as methyl 2-cyanomethacrylate, propyl 2-cyanoacrylate, isopropyl 2-cyanoacrylate, butyl 2-cyanoacrylate, isopropyl 2-cyanomethacrylate, cyclohexyl 2-cyanoacrylate, allyl 2-cyanoacrylate, and benzyl 2-cyanomethacrylate, may be used. These 2-cyano(meth)acrylates can be used alone or in combinations of two or more. In a preferred embodiment of the invention, the polymerizable monomer is ethyl 2-cyanoacrylate. Another preferred monomer is methyl 2-cyanoacrylate (cyanoacrylic acid methyl ester), also known as Coapt, Adhere, Cyanolit, Mecrilat, Mecrilate, mecrylate, and so on. It is commercially available from a number of suppliers in the U.S. and abroad. Unless the context indicates otherwise, the term "polycyanoacrylate" refers to a polymer formed from one or more of the above monomers.

Example 1—Process for Making Polycyanoacrylate Polymer

A mist of water droplets is created in a stainless steel-lined reaction chamber having a volume of approximately 8 cubic feet. Then, 500 grams of ethyl 2-cyanoacrylate is slowly dripped into the mist, producing an exothermic reaction. Polymer created by the reaction coats the inner walls of the reaction chamber. The rate of addition of the ethyl 2-cyanoacrylate is decreased or temporarily halted if the temperature in the reaction vessel reaches 50° C. After all of the ethyl 2-cyanoacrylate has been added, the reaction mass is allowed to cool for about 10 minutes to ensure that the final product temperature remains below 50° C. Any condensed water is then poured out, leaving a gummy or taffy-like substance adhering to the walls of the reaction chamber. The substance is scraped out of the container and pressed between two stainless steel plates each having an area of approximately 2 square feet to express water from the substance (polymeric mass). Subsequently, the polymeric mass is placed into an environmentally-controlled chamber for approximately 1 to 2 days at about 60° C., resulting in a dry solid polymeric mass.

Example 2—Process for Producing Powdered Polycyanoacrylate Product

The polymeric mass is then transferred into a burr grinder, where it reduced to a powder having a particle diameter in the range of from 1 to 200 microns, with a median particle diameter of approximately 20 microns and a mean particle diameter of approximately 60 microns.

Samples of product of the invention produced in accordance with the above method were analyzed by Microbac Laboratories (Hauser Division, Boulder, Colo., USA) via the following processes to determine various parameters of the particles, including the feret lengths and widths of the particles and the rectangularity of the particles:
1. Particle size distribution was measured using laser light scattering;
2. Skeletal density was determined via gas displacement density analysis;
3. Particle shape analysis was conducted using a dynamic image analyzer.

Results of feret length and width analysis and rectangularity determination were as follows:

| FERET LENGTH (sizes in microns) | | | |
|---|---|---|---|
| particle count | 12417 | number percentiles | |
| minimum | 8.0 | 10% | 17.1 |
| maximum | 260.3 | 25% | 21.5 |
| mean | 35.9 | 50% | 29.1 |
| std. dev. | 21.9 | 75% | 43.9 |
| mode | 25.2 | 90% | 62.6 |

| FERET WIDTH (sizes in microns) | | | |
|---|---|---|---|
| particle count | 12417 | number percentiles | |
| minimum | 5.7 | 10% | 10.6 |
| maximum | 158.2 | 25% | 13.4 |
| mean | 23.4 | 50% | 18.1 |
| std. dev. | 15.5 | 75% | 27.8 |
| mode | 16.0 | 90% | 43.4 |

| RECTANGULARITY | | | |
|---|---|---|---|
| particle count | 12416 | number percentiles | |
| minimum | 0.335 | 10%: | 0.662 |
| maximum | 1.000 | 25%: | 0.692 |
| mean | 0.718 | 50%: | 0.720 |
| std. dev. | 0.051 | 75%: | 0.747 |
| mode | 0.710 | 90%: | 0.774 |

Figure 1B:
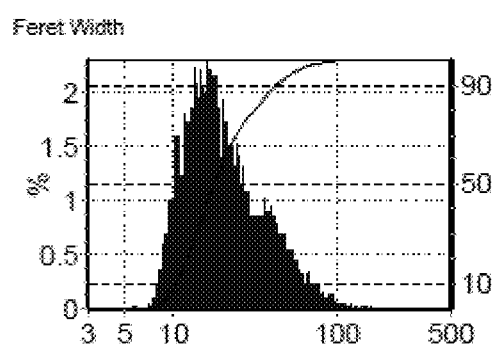
Figure 1C:
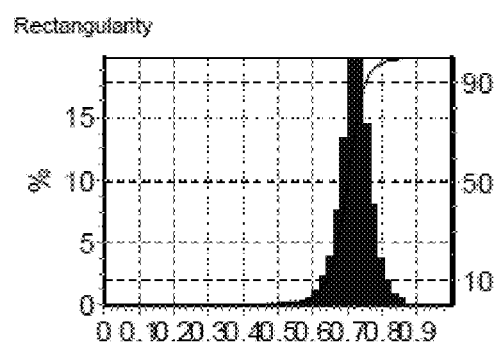

FIGS. 1A, 1B, and 1C are graphical depictions of, respectively, the above data relating to feret length, feret width, and rectangularity of the sample of particles produced in accordance with the invention.

An embodiment of the present invention is a powdered polycyanoacrylate polymer having the following particle size characteristics: (i) at least 50 weight-% of the powder particles have a feret length of from 20 to 80 nanometers; (ii) at least 50 weight-% of the powder particles have a feret width of from 10 to 40 nanometers; and (iii) at least 50 weight-% of the powder particles have a rectangularity ranging from 60 to 75.

Figure 2:
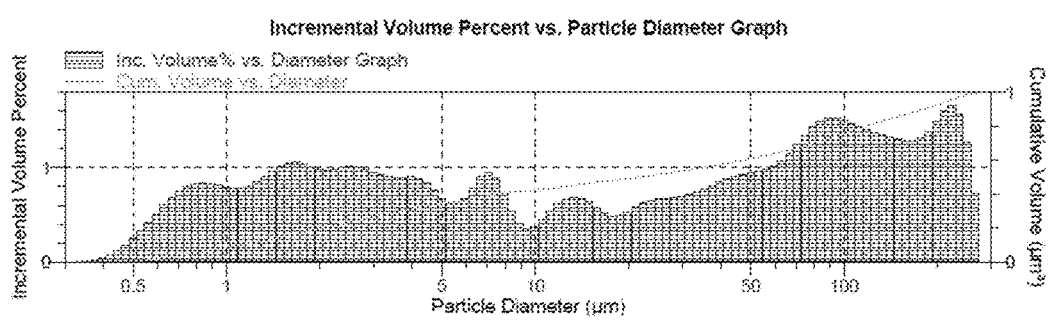
FIG. 2 is a graph of incremental volume percent versus particle diameter of a sample of the particles of the invention.

FIG. 2 is a graph of incremental volume percent versus particle diameter of a sample of the particles of the invention. The particles were made into a paste by mixing them with water and immersing the mixture in a Triton X ultrasonic bath for 2 minutes. Analysis conditions were as follows: flow rate 12.0 liters per minute, ultrasonic intensity 100%, ultrasonic time 240 seconds, and circulation time 240 seconds. The mean particle diameter was 58.269 microns. However, the median particle diameter was 21.783 microns.

Example 3—Method of Using the Powdered Polycyanoacrylate Product to Detect Fingerprints An example of a method of using the powdered polycyanoacrylate polymer is as follows:
1. Weigh out 0.04-0.12 grams of powder per cubic foot of fuming space and place it in an aluminum fuming dish;
2. Place the fuming dish on the a plate within the fuming chamber;
3. Set the fuming chamber relative humidity to 80%;
4. Turn the hot plate to 220° C. and set the run time to between 13 and 30 minutes; and
5. When the run is completed, photograph, lift, or otherwise process prints using standard fingerprint collection methods.

The powdered form of polycyanoacrylate made available by the present invention facilitates significant improvement in accurate weighing and measuring by the user when the product is used to detect fingerprints. The powder can more effectively be measured by weight using conventional methods, while posing little or no threat of exposure to fumes for the user. In its powdered form, the inventive product is unreactive at ambient temperatures, posing no handling exposure risks and emitting no discernable odors.

Due to its efficiency in dissipation of fumes, the invention allows for using only about one tenth the amount by volume during processing as compared to liquid cyanoacrylate processing. Additionally, once the heat source is removed and the temperature drops below 220° C., fuming stops immediately and all remaining polycyanoacrylate material can be collected and reused at a later date, further reducing waste.

Figure 3A:
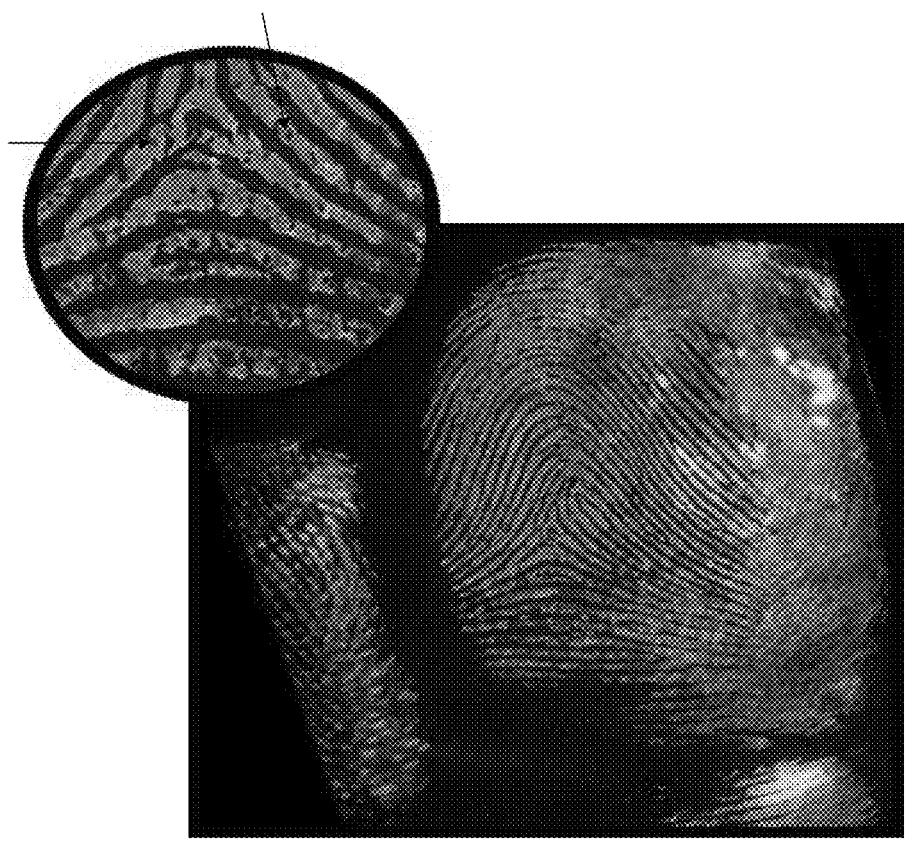
FIG. 3A is a photograph of a fingerprint developed with a composition of the present invention, showing first, second, and third level (pores) detection.
Figure 3B:
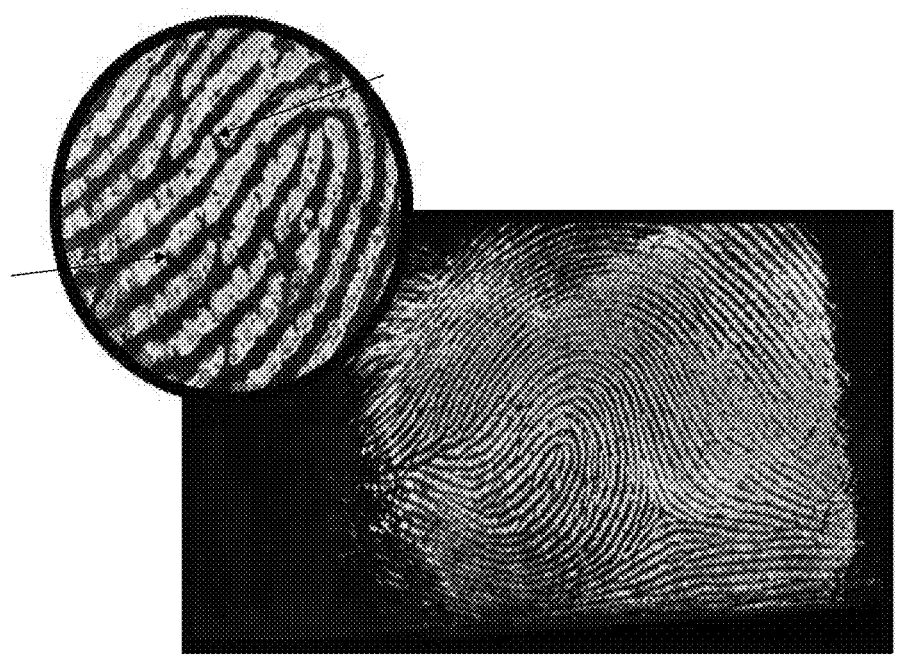
FIG. 3B is a photograph of a different fingerprint developed with a composition of the present invention, showing first, second, and third level (pores) detection.

FIGS. 3A and 3B are photographs of two different fingerprints, each of which was developed with a composition of the present invention. The photographs contain enlarged insets that serve to elucidate the fact that compositions of the present invention facilitate the visualization of pores (some of which are indicated by directional arrows in the insets) in the fingerprint ridges. Applicants' invention when used in accordance with the method outlined above consistently enables visualization of the pores as well as the ridges, thus enabling greater accuracy in fingerprint matching.

Example 4—Process for Producing Powdered Polycyanoacrylate Product from Methyl 2-Cyanoacrylate Monomer A mist of water droplets is created in a stainless steel-lined reaction chamber having a volume of approximately 8 cubic feet. Then, 500 grams of methyl 2-cyanoacrylate is slowly dripped into the mist, producing an exothermic reaction. Polymer created by the reaction coats the inner walls of the reaction chamber. The rate of addition of the methyl 2-cyanoacrylate is decreased or temporarily halted if the temperature in the reaction vessel approaches the boiling point of the methyl 2-cyanoacrylate. After all of the methyl 2-cyanoacrylate has been added, the reaction mass is allowed to cool for about 10 minutes to ensure that the final product temperature remains below the boiling point of the methyl 2-cyanoacrylate. Any condensed water is then poured out, leaving a gummy or taffy-like substance adhering to the walls of the reaction chamber. The substance is scraped out of the container and pressed between two stainless steel plates each having an area of approximately 2 square feet to express water from the substance (polymeric mass). Subsequently, the polymeric mass is placed into an environmentally-controlled chamber for approximately 1 to 2 days at about 60° C., resulting in a dry solid polymeric mass. The polymeric mass is then transferred into a burr grinder, where it reduced to a powder having a particle diameter in the range of from 1 to 200 microns, with a median particle diameter of approximately 20 microns and a mean particle diameter of approximately 60 microns.

Particular embodiments of the present invention have been described in detail above. However, it will be apparent that variations and modifications of the described embodiments are possible. Accordingly, the scope of the present invention is not limited to the embodiments described but instead is limited only by the appended claims.

What is claimed is:

1. A powdered polycyanoacrylate polymer produced by a process comprising:
    (a) charging a reaction vessel with a mist comprising water;
    (b) dripping methyl or ethyl 2-cyanoacrylate into the water mist in the reaction vessel, thereby producing an exothermic reaction, thereby conducting uniform polymerization of said methyl or ethyl 2-cyanoacrate, and temporarily halting or decreasing a rate of addition of methyl or ethyl 2-cyanoacrylate if the temperature in the reaction vessel becomes too high for uniform polymerization;
    (c) once polymerization of the methyl or ethyl 2-cyanoacrylate is complete, allowing the reaction mass to cool;
    (d) removing polycyanoacrylate polymer formed in step (b) and cooled in step (c) from the reaction vessel;
    (e) drying the polycyanoacrylate polymer to provide a dry solid polycyanoacrylate polymer; and
    (f) pulverizing the dry solid into a powder, wherein more than 95% of the particle mass in said powder comprises particles having a particle diameter in the range of from 1 to 200 microns, or wherein the particles in said powder have one or more of the following particle size characteristics (i), (ii), and (iii): (i) at least 50 weight-% of the powder particles have a feret length of from 20 to 80 nanometers; (ii) at least 50 weight-% of the powder particles have a feret width of from 10 to 40 nanometers; (iii) at least 50 weight-% of the powder particles have a rectangularity ranging from 60 to 75.

2. The powdered polycyanoacrylate polymer of claim 1, wherein more than 95% of the particle mass comprises particles having a particle diameter in the range of from 1 to 200 microns.

3. The powdered polycyanoacrylate polymer of claim 2, having a median particle diameter of 10-30 microns and a mean particle diameter of 30-90 microns.

4. The powdered polycyanoacrylate polymer of claim 3, having a median particle diameter of approximately 20 microns and a mean particle diameter of approximately 60 microns.

5. The powdered polycyanoacrylate polymer of claim 1, wherein the rate of addition of methyl or ethyl 2-cyanoacrylate in step (b) is temporarily halted or decreased if the temperature in the reaction vessel reaches 45-55° C.

6. The powdered polycyanoacrylate polymer of claim 1, wherein the rate of addition of methyl or ethyl 2-cyanoacrylate in step (b) is temporarily halted or decreased if the temperature in the reaction vessel becomes higher than 50° C.

7. The powdered polycyanoacrylate polymer of claim 1, wherein the monomer which is polymerized to make said powdered polycyanoacrylate polymer is ethyl 2-cyanoacrylate.

* * * * *